United States Patent [19]

Juvinall et al.

[11] Patent Number: 4,958,223
[45] Date of Patent: Sep. 18, 1990

[54] INSPECTION OF CONTAINER FINISH

[75] Inventors: John W. Juvinall, Ottawa Lake, Mich.; Robert C. Redmond, Toledo, Ohio

[73] Assignee: Owens-Brockway Glass Container Inc., Toledo, Ohio

[21] Appl. No.: 448,531

[22] Filed: Dec. 11, 1989

Related U.S. Application Data

[62] Division of Ser. No. 245,236, Sep. 16, 1988.

[51] Int. Cl.$^5$ .......................................... H04N 5/335
[52] U.S. Cl. .................................. 358/106; 358/101
[58] Field of Search ............... 358/93, 101, 106, 107, 358/213, 29; 382/8; 250/223 B

[56] References Cited

U.S. PATENT DOCUMENTS

| | | | |
|---|---|---|---|
| 4,230,219 | 10/1980 | Pezzin | 198/480.1 |
| 4,378,493 | 3/1983 | Dorf | 250/223 B |
| 4,378,494 | 3/1983 | Miller | 358/106 |
| 4,378,495 | 3/1983 | Miller | 358/106 |
| 4,430,673 | 2/1984 | Salomon | 358/213.27 |
| 4,492,476 | 1/1985 | Miyazawa | 250/223 B |
| 4,679,075 | 7/1987 | Williams | 358/106 |
| 4,701,612 | 10/1987 | Sturgill | 358/106 |
| 4,831,250 | 5/1989 | Fukuchi | 250/223 B |

Primary Examiner—Howard W. Britton

[57] ABSTRACT

Apparatus for inspecting the finish of a container as the container is held and rotated about its central axis. A light source is positioned to direct diffused light energy onto the container finish, and a camera is positioned across the axis of the container from the light source. The camera comprises multiple arrays of light sensitive elements positioned with respect to the camera focusing elements on a common optical plane opposed to the light source to receive non-overlapping images of the container finish spaced from each other laterally of the container axis. Information processing electronics are coupled to the camera arrays for indicating optical characteristics of the container finish as differing functions of light intensity incident on the elements of each array. In the various disclosed embodiments of the invention, the arrays comprise one or more linear or matrix arrays for receiving non-overlapping images of the container finish at preselected orientation with respect to each other for detecting structural commercial variations and/or geometric parameters of the container finish.

12 Claims, 4 Drawing Sheets

FIG.6

INSPECTION OF CONTAINER FINISH

This is a division of application Ser. No. 07/245,236 filed Sept. 16, 1988.

The present invention is directed to optical imaging apparatus having particular utility for inspection of transparent containers, and more specifically to an apparatus and method for inspecting the finish of containers for commercial variations and geometric characteristics.

BACKGROUND OF THE INVENTION

In the art of container manufacture, the term "container finish" generally refers to that portion of the container which defines the container mouth. In a bottle, for example, the finish includes that portion of the container neck having threads and/or shoulders for receiving the container cap, as well as the upper surface of the neck surrounding the container mouth against which the cap seats. It is important that the container finish be properly manufactured so that a cap may be affixed thereto to seal the container cavity against leakage and escape of carbonation during handling and storage.

Conventional technology for mass production of glass or plastic containers involves forming the containers in a multiplicity of blow-molds Various types of faults or checks, termed "commercial variations" in the art, may occur. It has heretofore been proposed to employ optical scanning techniques for inspecting such containers for variations which affect optical transmission characteristics of the container sidewall In U.S. Pat. Nos. 4,378,493, 4,378,494 and 4,378,495, all of which are assigned to the assignee of the present application, there are disclosed methods and apparatus in which glass containers are conVeyed through a plurality of stations where they are physically and optically inspected. At one inspection station, a glass container is held in vertical orientation and rotated about its vertical axis. An illumination source directs diffused light energy through the container sidewall. A camera, which includes a plurality of light sensitive elements or pixels oriented in a linear array parallel to the vertical axis of container rotation, is positioned to view light transmitted through a vertical strip of the container sidewall. The output of each pixel is sampled at increments of container rotation, and event signals are generated when adjacent pixel signals differ by more than a preselected threshold level. An appropriate reject signal is produced and the rejected container is sorted from the conveyor line.

U.S. Pat. No. 4,701,612, assigned to the assignee hereof, discloses a method and apparatus for inspecting the finish of transparent containers, particularly glass containers, which include facility for directing diffused light energy laterally through the container finish as the container is rotated about its central axis. A camera includes a plurality of light sensitive elements or pixels disposed in a linear array angulated with respect to the container axis and coplanar therewith to view the external and internal finish wall surfaces, the latter through the open container mouth. Individual elements of the camera linear array are sampled by an information processor at increments of container rotation, and corresponding data indicative of light intensity at each element is stored in an array memory as a combined function of element number and scan increment. Such data is compared following completion of container rotation to standard data indicative of an acceptable container finish, and a reject signal is generated if such comparison exceeds an operator-adjustable threshold. Although the method and apparatus so disclosed represent a significant advance in previous finish inspection techniques and have enjoyed acceptance in the art, improvement remains desirable. For example, the method and apparatus so disclosed, while highly effective in detecting horizontal variations in the container finish, are not as effective in detecting vertical and radial variations. Furthermore, the disclosed apparatus cannot measure geometric characteristics of the container finish such as inside diameter, outside diameter or thread diameter.

U.S. Pat. No. 4,492,476 discloses an optical inspection system for transparent containers in which an image of a test container is directed onto an array camera which includes a two-dimensional CCD image sensor. Sensor elements or pixels are scanned by column parallel to the container axis, and circuitry is responsive to detection of the image edges for identifying an inspection region containing the container image, and for processing image data for variation detection only within such inspection region. However, all image data must be scanned for identifying the inspection region. Furthermore, image data processing is accomplished entirely at the processing circuitry. As a result, the disclosed technique is more time consuming than desirable for inspecting containers in a mass production environment. Moreover, the disclosed system does not measure geometric characteristics of containers.

U.S. Pat. No. 4,430,673 discloses an optical star tracker for spacecraft attitude control which employs a CCD image sensor and control electronics for scanning and selectively processing image data. In particular, only information from sensor pixels in an area of interest are subject to a/d conversion and processing, the remaining data being clocked from the sensor pixels but ignored. Again, all image data processing is carried out at the electronics.

OBJECTS AND SUMMARY OF THE INVENTION

It is therefore a general object of the present invention to provide optical imaging apparatus and method having particular utility for inspecting the finish of a container as a function of optical characteristics thereof, and for indicating that the container under inspection should be rejected when such optical characteristics do not meet a predetermined standard.

A more particular object of the invention is to provide a container finish inspection apparatus and method of the described character which address and overcome the aforementioned deficiencies in the art, which is adapted for detection of commercial variations of any orientation, and which are also capable of measuring geometric characteristics of the container finish.

A further object of the invention is to provide container finish inspection apparatus of the described character which is readily adjustable for inspection of containers having differing finish sizes.

In accordance with one aspect of the present invention, and as applied specifically to inspection of the finish of transparent containers, apparatus of the type disclosed in above-referenced U.S. Pat. No. 4,701,612 is characterized in that the camera comprises at least first and second arrays of light sensitive elements positioned with respect to the camera focusing elements on a common optical plane opposed to the diffused light source across the container finish so as to receive nonoverlapping images of the container finish spaced from each other laterally of the container axis of rotation. The information processor is coupled to each of the arrays for indicating optical characteristics of the container finish as differing functions of light intensity incident on the elements of each array. In one embodiment of the invention, the first and second arrays comprise matrix arrays which receive two-dimensional images of laterally opposite side portions of the container finish, and a linear third array of light sensitive elements is positioned so as to receive a one-dimensional image of the container finish positioned between the two-dimensional images and coplanar with the container axis.

In accordance with another aspect of the invention, at least three and preferably five linear arrays are formed and positioned with respect to the camera focusing elements for receiving respective parallel one-dimensional images of the container finish, one of which is coplanar with the container axis of rotation and the others of which are spaced in pairs on laterally opposed sides of such axis. In one embodiment, five separate linear arrays receive parallel one-dimensional images of the container finish through camera focusing elements which include mirrors coupled to servo motors for selectively positioning the one-dimensional images laterally of the container axis. In another embodiment, the camera comprises a unitary matrix array such as a CCD image sensor which receives a two-dimensional image of the entire container finish, and electronic processing circuitry coupled to the matrix array for selectively processing information from separate array elements and thereby functionally dividing the unitary matrix array into a plurality of parallel linear arrays spaced from each other laterally of the container axis.

Thus, in accordance with yet another aspect of the invention, a matrix array image sensor of generally conventional construction is coupled to scan control and data processing electronics for selectively reading image pixel data of interest, and for effectively ignoring other data. Furthermore, the scan control electronics interacts with the image sensor in such a way that at least some signal processing may be carried out at the sensor. The latter feature in particular reduces processing required at the data processing electronics and increases accuracy. Multiple scan control clocks are employed for rapidly clocking ignored data, while clocking data of interest at a slower rate compatible with the image data processing electronics.

BRIEF DESCRIPTION OF THE DRAWINGS

The invention, together with additional objects, features and advantages thereof, will be best understood from the following description, the appended claims and the accompanying drawings in which:

DETAILED DESCRIPTION OF PREFERRED EMBODIMENTS

Figures 1, 2:
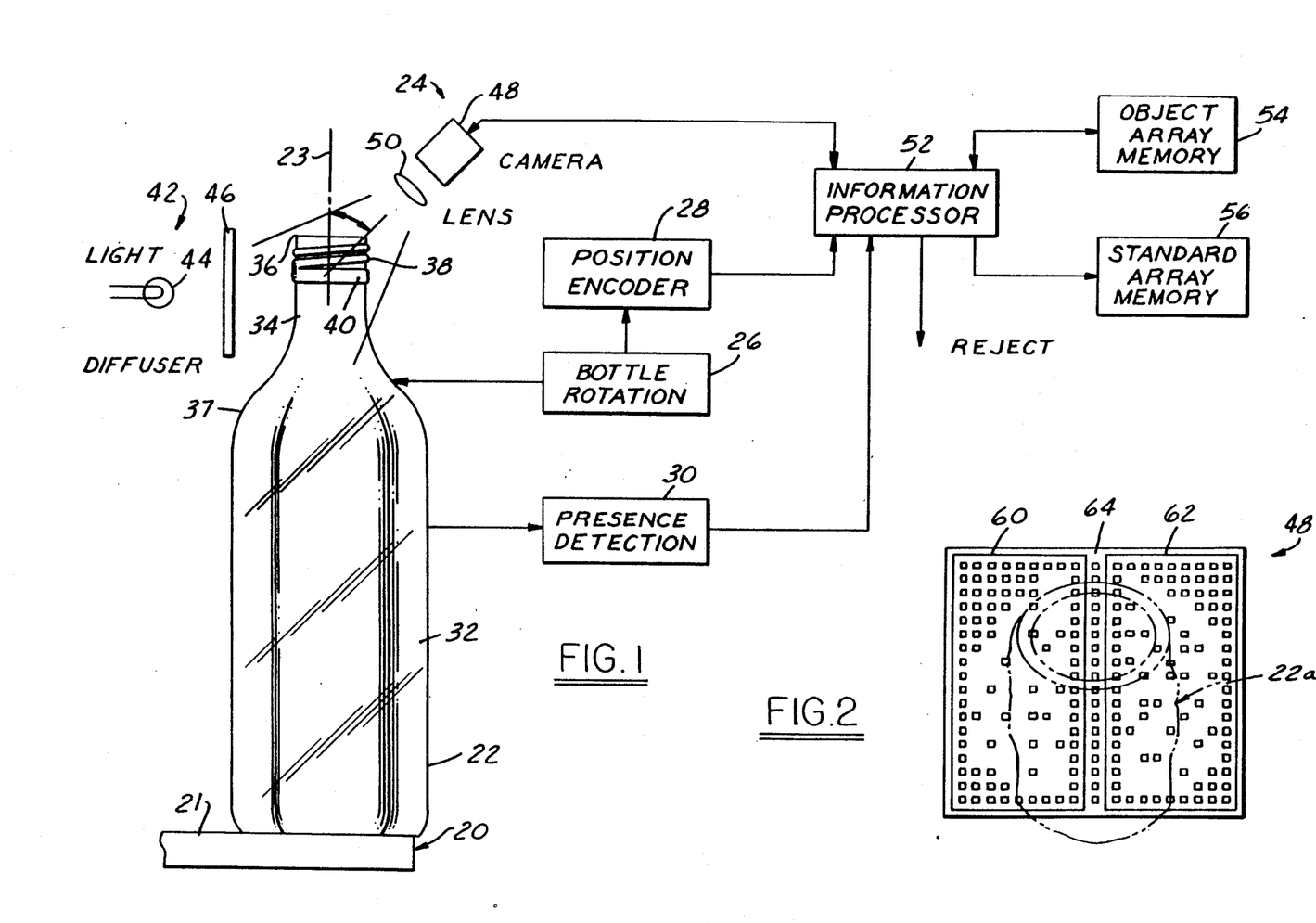
FIG. 1 is a schematic diagram of apparatus for inspecting the finish of containers in accordance with the present invention.
FIG. 2 is a schematic illustration of the container finish as viewed by the camera of FIG. 1, with camera field of view superimposed thereon, in accordance with a first embodiment of the invention.

Referring to FIG. 1, a conveyor 20, typically including a starwheel (not shown) and a slide plate 21, is so disposed and connected to a source of molded containers as to bring successive containers 22 into position at a finish inspection station 24. Conveyor 20 may be of any suitable type, such as those shown in U.S. Pat. Nos. 4,230,219 and 4,378,493, the disclosures of which are incorporated herein by reference, and would typically include a rotatable starwheel for bringing successive containers into position and holding the containers in fixed position during the scanning operation. A bottle rotating device 26, such as a drive roller, is positioned to engage container 22 at station 24 and to rotate the container about its central axis 23. An encoder 28 is coupled to the container rotation mechanism to provide signals indicative of increments of container rotation. A detector 30, such as a limit switch, is positioned to provide a signal indicative of presence of container 22 at station 24.

In the preferred implementation of the invention herein discussed, container 22 is illustrated as a molded glass bottle having a container body 32 and a generally cylindrical neck 34 which projects upwardly from the body shoulder 37. The finish portion of the container inspected in accordance with the present invention includes the upper portion of neck 34 which terminates in a cap sealing surface 36. A helical thread 38 is integrally molded onto the outer surface of the finish wall which surrounds the container mouth, and a lip or shoulder 40 is likewise formed on the finish wall outer surface over which a cap skirt may be crimped in the usual manner for affixing the cap to the container. In general, the present invention is disclosed in conjunction with apparatus adapted to inspect that portion of the container finish to which the cap is to be affixed.

A light source 42 is positioned to direct diffused light energy onto the container finish from a direction generally lateral to container axis 23. Light source 42 includes one or more lamps 44 and a diffuser plate 46. A camera 48 is positioned on the side of axis 23 opposite to light source 42 to receive an image of the container finish through the camera lens 50. An information processor 52 receives a signal from detector 30 indicative of presence of a container 22 at inspection station 24, and signals from encoder 28 indicative of increments of container rotation Camera 48 is likewise coupled to information processor 52 for receiving scan control signals and providing signals indicative of the intensity of light incident on each camera element Information processor 52 is connected to an object array memory 54 and to a standard array memory 56, and has an output for providing a reject signal to container sorting apparatus (not shown). Each array memory 54, 55 is an N×M array memory, where N is equal to or greater than the number of elements or pixels in camera 48, and M is equal to or greater than the number of scan increments for one complete rotation of container 22. To the extent thus far described, inspection station 24 is similar to that illustrated in U.S. Pat. No. 4,701,612, the disclosure of which is incorporated herein by reference.

In accordance with a first embodiment of the present invention illustrated schematically in FIG. 2, cameras 48 comprises three separate arrays 60, 62, 64 of light sensitive pixels or elements carried on a common support or substrate 66. Arrays 60, 62 are two-dimensional or matrix arrays positioned on opposite lateral sides (with respect to the container axis) of the one-dimensional or linear element array 64. Lens 50 focuses the fields of view of camera arrays 60–64 (or, conversely, focuses the image 22a of container 22 onto the camera arrays) in the manner illustrated in FIG. 2 so as to view diametrically opposite portions of the coaxial cylindrical container finish external and internal wall surfaces, the internal wall surface being viewed at an angle through the open container mouth. The fields of view of matrix arrays 60, 62 extend from the central portion of the container finish laterally outwardly so as to overlie opposite side portions of the container finish. Each array 60, 62 and 64 is individually connected to information processor 52 for selective control of array scanning by information processor 52, and for selective receipt and processing of signals indicative of light intensity received at the individual array elements Linear array 64 may comprise 512 elements having a composite linear or one-dimensional field of view which extends at least from the opposite edge of the finish sealing surface to the adjacent lower edge of shoulder 40. Matrix arrays 60, 62 may comprise 128×256 element arrays.

As previously indicated, and as described in greater detail in U.S. Pat. No. 4,701,612, incorporated by reference above, processing of signals from central linear array 64 and comparison of object array data in memory 54 to standard data in memory 56 is effective for detecting horizontally oriented checks or faults in the container finish However, vertical checks and radial checks in the container finish, which are essentially coplanar with the one-dimensional image of array 64, are not as reliably detected. Furthermore, geometric parameters of the container finish, such as neck inside diameter and outside diameter, thread outside diameter, thread root diameter and thread contour, cannot be determined using array 64 alone. However, all of such checks and parameters can be readily detected or measured by scanning matrix arrays 60, 62 at increments of container rotation, storing such information in object array memory 54 and then comparing such information to data stored in standard memory 56 following completion of a scan operation. For example, finish diametric characteristics are measured as a function of the number of elements in matrix arrays 60, 62 in each lateral row which receive the shadow or image of the container finish (It will be appreciated that matrix arrays 60, 62 are positioned on substrate 66 so that the rows of each matrix are in lateral alignment and the columns of each matrix are at predetermined separation from each other.) Resolution of variation detection and geometric parameter measurement depend upon, and may be correspondingly controlled as a function of, the number of and separation between elements in arrays 60–64 and the number of scan increments detected by encoder 28 per container revolution.

Figures 3, 5:
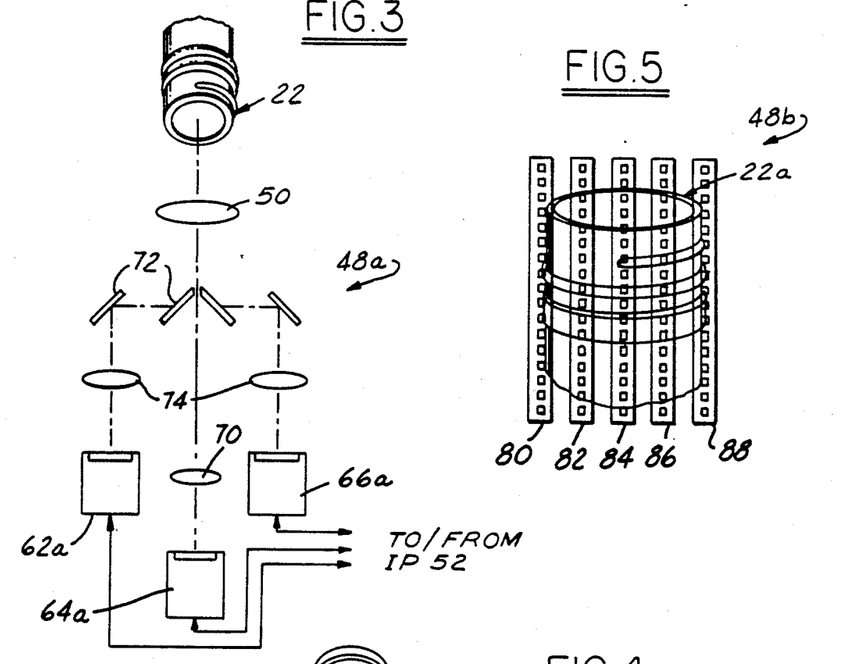
FIG. 3 is a fragmentary schematic diagram of a camera arrangement in accordance with a second embodiment of the invention.
FIG. 5 is a view similar to that of FIG. 2 and showing the camera field of view in the embodiment of FIG. 4.

FIG. 3 illustrates a modified camera arrangement 48a which comprises a linear array camera 64a and separate matrix array cameras 62a, 66a, all of which are of conventional construction. A central one-dimensional image of the finish of container 22 is received from lens 50 and focused onto array camera 64a by the lens relay 70. The lateral two-dimensional images of the container finish are projected onto matrix cameras 62a, 66a by the folding mirrors 72 and the corresponding relay lenses 74. Thus, the field of view of camera arrangement 48a is identical to that illustrated schematically in FIG. 2. The embodiment of FIG. 3 has the advantage as compared with the embodiment of FIG. 2 of using standard matrix and linear array cameras 62a–66a, and is thus more economical to implement. Another advantage of the embodiment of FIG. 3 (which may also be employed in the embodiment of FIGS. 1 and 2) is that the separate matrices may be connected to individual preprocessors for initially processing pixel information and then feeding the same to a central processor. In this way, measurement time and resolution may be increased significantly.

Figure 4:
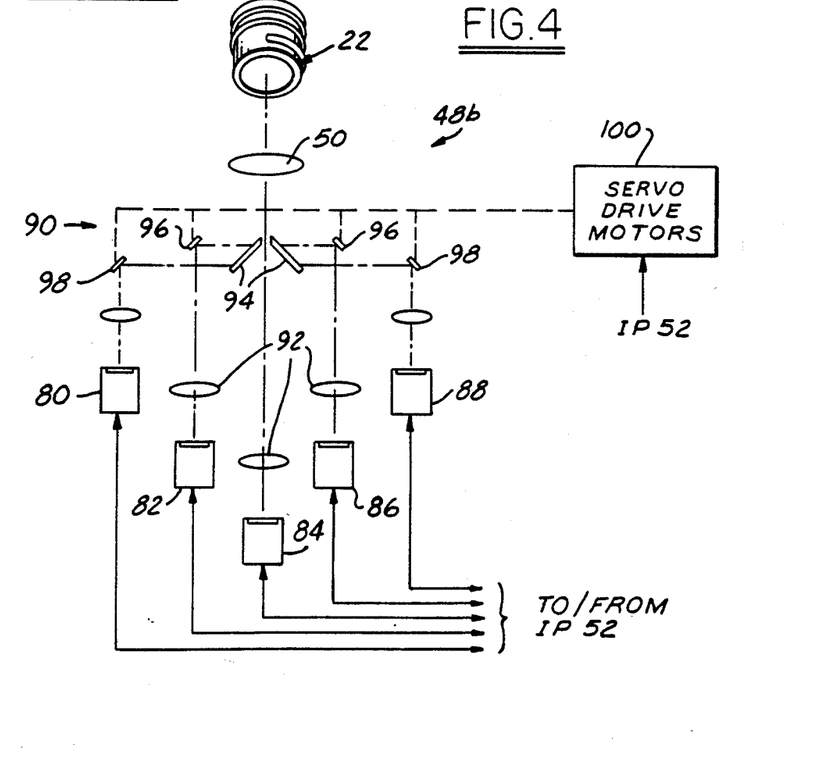
FIG. 4 is a fragmentary schematic diagram of another camera arrangement in accordance with the present invention.

FIGS. 4 and 5 illustrate a second modified camera arrangement 48b (FIG. 4) and its corresponding field of view with respect to the container finish (FIG. 5). In the embodiment of FIG. 4, camera 48b comprises five linear array cameras 80, 82, 84, 86 and 88 which receive corresponding respective parallel one-dimensional images of the finish of container 22 through primary lens 50, an arrangement 90 of folding mirrors and the respective secondary or relay lenses 92. That is, the one-dimensional image received by central camera 84 is fed directly from primary lens 50 through the aperture between mirrors 94 and corresponding relay lens 92 onto the camera array. The images directed to intermediate cameras 82, 86 are folded by mirrors 94 and 96 through corresponding lenses 92 onto the camera arrays, while the one-dimensional images received by outside cameras 80, 88 are folded by mirrors 94 and mirrors 98 through lenses 92 onto the camera arrays. The fields of view of cameras 80–88 with respect to the container finish image 22a are illustrated in FIG. 5. The image at central array 84 is coplanar with the container finish axis, and thus corresponds to the image of linear array 64 in FIG. 2. The images at arrays 80, 88 are received from the outside edges of the container finish. The images at intermediate arrays 82, 86 are respectively positioned midway between outer array images 80, 88 and central image 84. Thus, central array 84 is employed to detect horizontal variations in the manner previously discussed, intermediate arrays 82, 86 are employed to detect vertical variations, radial variations and LOF variations, and outer arrays 80, 88 are employed to determine geometric characteristics of the container finish.

In accordance with another feature of the embodiment of the invention illustrated in FIG. 4, each of the folding mirrors 96, 98 is carried on a corresponding mirror-mount which is individually coupled to a corresponding servo drive motor, illustrated collectively at 100. Drive motors 100 receive drive control signals from information processor 52 (FIG. 1) for controlled adjustable positioning of mirrors 96, 98, and thereby adjustably positioning the fields of view of linear array cameras 80, 82, 86 and 88 with respect to the container finish image. Thus, the array fields of view may be readily adjusted for container finishes of differing sizes or geometries. Furthermore, at least some diametric characteristics of the container finishes may be determined as a function of position of the servo motors coupled to outside mirrors 98. Most preferably, mirrors 96, 98 move together to accommodate container wobble.

Figure 6:
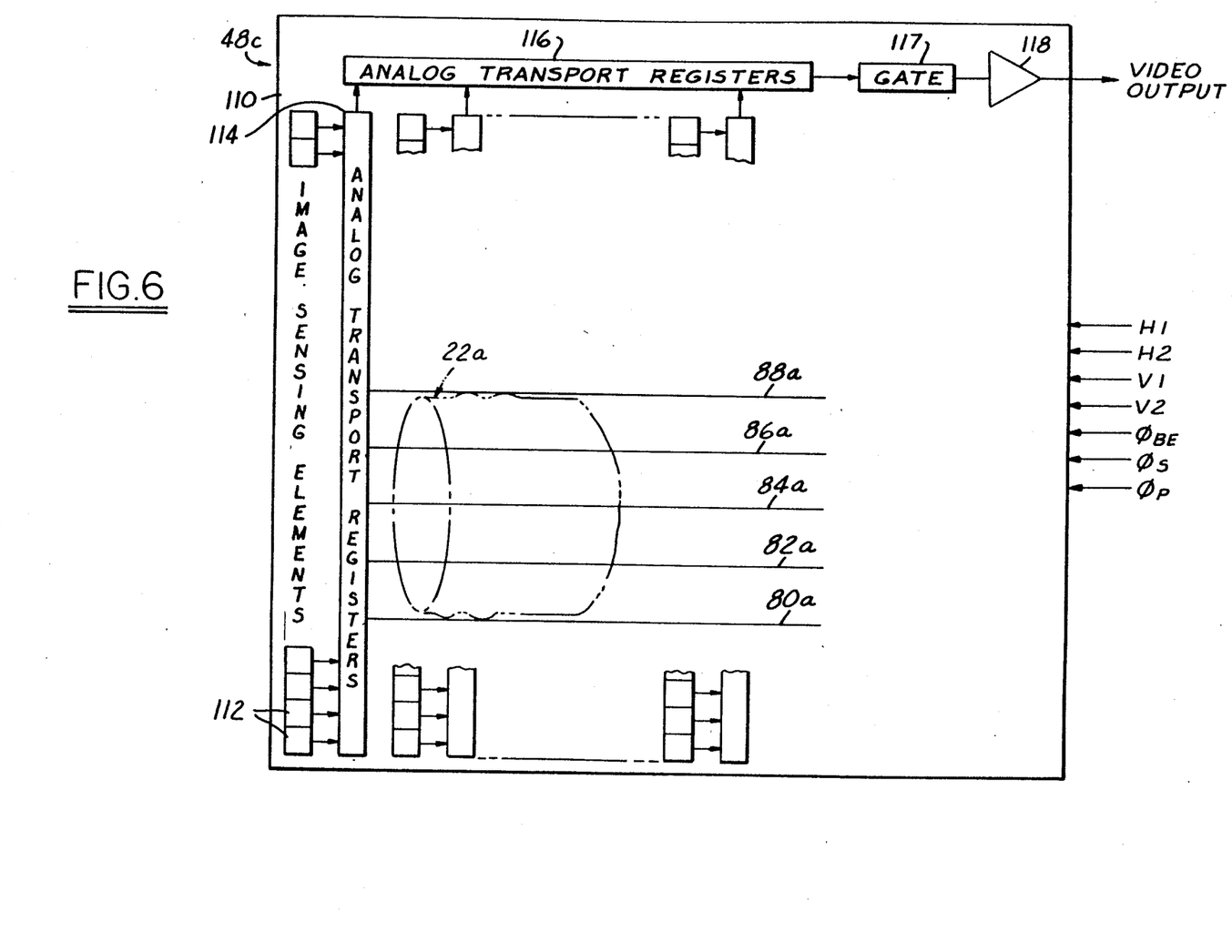
FIG. 6 is a fragmentary schematic illustration of the container finish as viewed by the camera in accordance with yet another embodiment of the invention, with effective camera field of view superimposed on the container finish.
Figure 7:
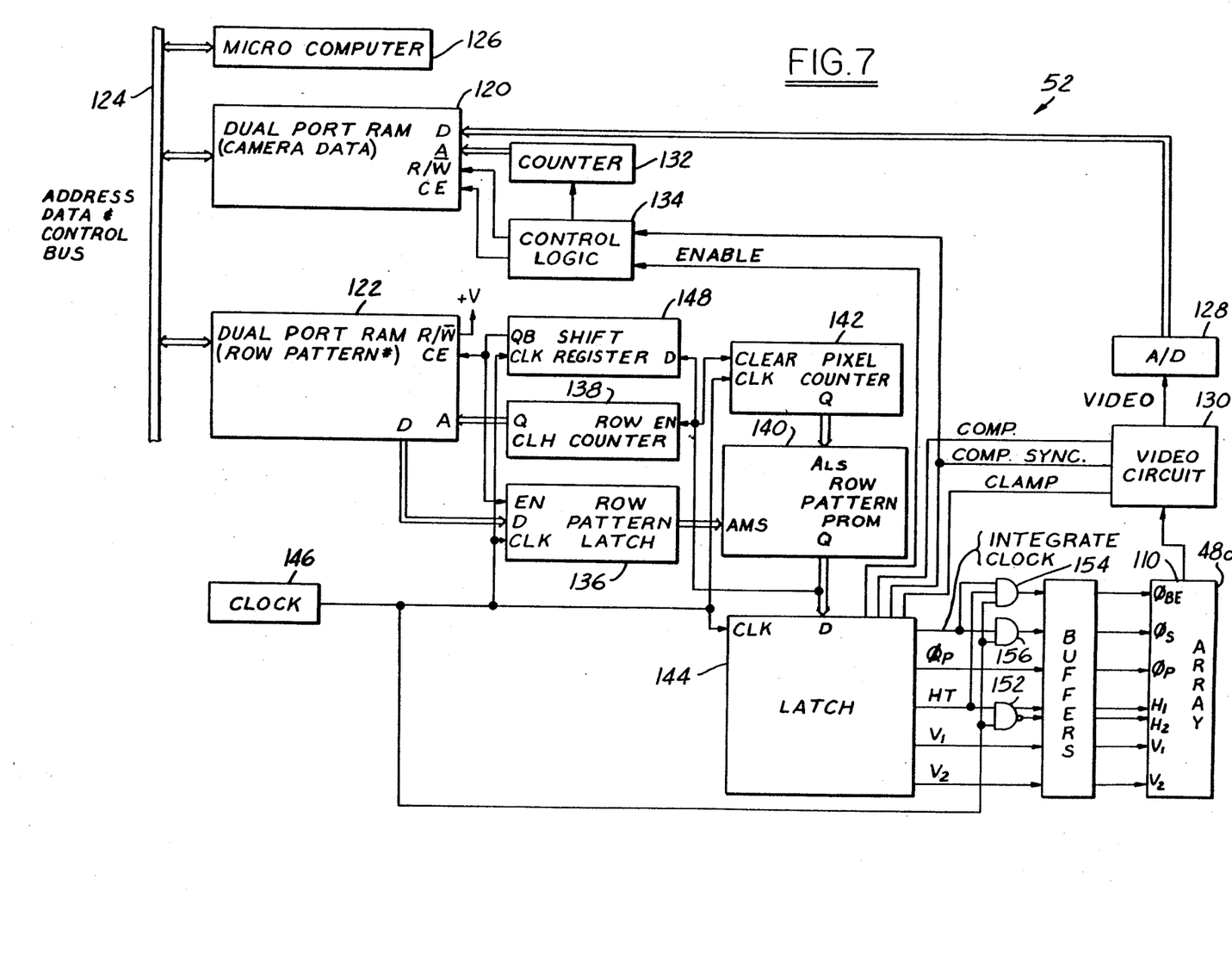
FIG. 7 is a functional block diagram of scan control and data processing electronics employed in conjunction with the camera arrangement of FIG. 6.

FIGS. 6 and 7 illustrate a presently preferred embodiment of the invention in which the camera 48c comprises a monolithic matrix array sensor 110, preferably a solid-state charge coupled device having on-board processing electronics. In a working embodiment of the invention, sensor 110 comprises a Fairchild CCD222 488×380 element Area Image Sensor illustrated in a Product Data Sheet of the same title (1982) which is incorporated herein by reference. Schematic representations and signal designations illustrated in FIGS. 6 and 7 of the present application correspond to those employed by that manufacturer. It will be appreciated, of course, by persons skilled in the art, that the invention is in no way limited to such specific sensor. It will also be appreciated, for purposes of clarity, that sensor 110 is illustrated in typical orientation recognized by persons in the art, and will be so discussed hereinafter, with the finish image 22a horizontal rather than vertical. In practice, sensor 110 is rotated 90° clockwise from the orientation of FIG. 6 so that the "horizontal transport register" 116 (using conventional terminology) is oriented vertically, and the "vertical transport registers" 114 are oriented horizontally (orthogonal to the vertical container axis).

Image sensor 110 comprises a multiplicity of individual image sensing elements or pixels 112 disposed in columns orthogonal to the container finish axis. All sensing elements 112 of each column are connected to a corresponding analog transport register 114. The several analog transport registers 114 are correspondingly connected to an analog transport register 116, which is connected through a gate 117 and an amplifier 118 to provide video output to information processor 52 (FIGS. 1 and 7). Sensor 110 receives control signals from information processor 52. These control signals include clock signals H1 and H2 for controlling register 116, and clock signals V1 and V2 for controlling registers 114 for odd and even fields. A clock signal $\phi_{BE}$ provides bias to gate 117. A clock signal $\phi_P$ gates pixels 112 onto transport registers 114, and a clock signal $\phi_S$ is applied to the sample-and-hold control input of amplifier 118.

FIG. 7 is a functional block diagram of that portion of information processor 52 relating to control of camera 48c and receipt of data therefrom. A dual port camera data RAM 120 (which may be an array memory) and a dual port row pattern control RAM 122 have respective first sets of address and data ports connected by a bus 124 to a control microcomputer 126. RAM 120 has a second data port D coupled through an a/d converter 128 to the video circuit 130 which receives the video output of sensor 110. The second address port A of RAM 120 receives an input from a counter 132. Counter 132, and the read/write control input R/W and the enable input CE of RAM 120, are coupled to control logic 134. The second data port D of RAM 122 is connected to the data input D of a row pattern latch 136. A row counter 138 provides a counter output Q to the second address port A of RAM 122. A read control PROM 140, having row and column read control information prestored therein, receives least significant address bit information ALS from the output Q of a pixel counter 142, and receives most significant address bit information AMS from the output of row pattern latch 136. The output Q of PROM 140 is fed to a latch 144.

A master clock 146 provides input to latch 144, counter 142, latch 136 and a shift register 148. The most significant address bit at output Q of PROM 140 provides an enable input EN to counter 138, a clear input to counter 142 and a D input to shift register 148. The output QB of register 148 is fed to the enable input CE of RAM 122. Latch 144 provides the usual clamp, sync and blank control inputs to video circuit 130, as well as an enable input to central logic 134. Latch 144 also provides clock signals V1, V2 and $\phi_P$ to sensor 110 through a buffer 150. A horizontal toggle output HT of latch 144 is connected as an input to a pair of AND gates 152, 154. Gate 152 receives a second input from clock 146, and provides complementary outputs through buffer 150 to the H1 and H2 clock inputs of sensor 110, signals H1 and H2 thus being the inverse or complement of each other. Gate 154 receives a second input from clock 146 and an integrate clock control input from latch 144, and provides clock signal $\phi_{BE}$ to sensor 110 through buffer 150. A gate 156 receives the integrate clock control output from latch 144, a second input from clock 146, and provides clock signal $\phi_S$ to sensor 110 through buffer 150.

In general operation of sensor 110 with image processor 52, analog signals indicative of light intensities received at each of the image sensing elements 112 are fed to the corresponding analog transport register 114 under control of clock $\phi_P$. In standard applications of matrix image sensors 110, analog transport registers 114 are clocked by alternating fields onto register 116, and register 116 is clocked through gate 117 and amplifier 118 to the video processing electronics. Thus, in such standard video applications, signals corresponding to intensity of light received at the various image sensing elements would be fed row-by-row to and through register 116 to the video electronics. In accordance with an important feature of this embodiment of the invention, however, the various matrix scan control signals are selectively operated so as to highlight and transmit to image processor 52 only data from element rows or lines of interest—e.g. the five element lines corresponding to images 80-88 in FIG. 5—while ignoring data indicative of other element lines.

More specifically, and assuming that the onedimensional image 88a (FIG. 6) at the right-hand edge of the finish threads (corresponding to image 88 in FIG. 5) is at the tenth line of image sensing elements 112 (counting from the top-most line of image sensing elements), all elements 112 are first clocked onto registers 114 under control of signal $\phi_P$, and all registers 114 are rapidly cycled (V1 and V2 at high frequency) nine times so as to load the corresponding element image signals into transport register 116 where the nine signals from each column are effectively integrated. Transport register 116 is rapidly cycled by clock signals H1 or H2 but not read by the electronics. In this way, unwanted data is effectively ignored or dumped. Clocking at 32 MHz, for example, may exceed the capabilities of the processing electronics since the data is to be ignored. Transport registers 114 are then again clocked so as to load into register 116 the image data corresponding to image 88a at the tenth line of pixels 112. Transport register 116 is then clocked less rapidly—e.g., at 16 MHz—so as to download such image data through gate 117 and amplifier 118 to information processor 52 (FIG. 7) at a rate at which the data can be read and stored. This process is repeated for one-dimensional images 86a, 84a, 82a and 80a so that the five groups of image data are stored in information processor 52. By selectively scanning the image data in this manner, it will be appreciated that image scan time is significantly reduced as compared with scanning of the entire image For example, in a working embodiment of the invention of FIG. 6, scanning of images 80a-88a requires downloading of only one percent of the image data in a 512×512 matrix array, and requires only on the order of one millisecond of scanning time, as opposed to a normal frame of time 33.3 milliseconds. (Such working embodiment of the invention comprises a Fairchild CCD 3000 video camera with control logic modified as hereinabove described.) Furthermore, the amount of data read and stored is significantly reduced as compared with reading and analyzing all video data at array sensor 110.

A particularly significant feature of the embodiment of FIG. 6 lies in the fact that the signal-to-noise ratio of any of the five images 80a-88a may be significantly enhanced, with a corresponding decrease in resolution, by summing image information from a number of element lines within transport register 116 prior to downloading to information processor 52. For example, image 84a may be obtained by integrating or summing image data from several element lines on either side of the line at the geometric center of the container finish image This gives high sensitivity to horizontal commercial variations. This may be accomplished on sensor 110 by simply successively clocking such data onto transport register 116, which inherently integrates such data. The number of rows integrated must be less than the minimum size of the checks to be detected. (This procedure need not be employed in processing outer images 80a, 88a, which are essentially responsive to the white/black edge of the container finish image or shadow.) This feature of the invention thus employs or takes advantage of the inherent capability of sensor 110 to perform such integration as described while increasing signal-to-noise ratio. For example, integration of sixteen lines at sensor 110 provides four times the signal-to-noise ratio (assuming Gaussian noise) as would be the case if the integration were performed within information processor 52 (in addition to requiring less time both to obtain the data from the array and to perform the integration in processor 52). Similar integration may be performed at gate 117 to enhance vertical checks. This same procedure may be employed in obtaining intermediate images 82a and 86a. Thus, real time selective scanning control in the manner described, in which a portion of the information processing is actually performed at the sensor, increases both accuracy and efficiency of information processing.

Within information processor 52 (FIG. 7), row pattern information—e.g., row or line information to be rapidly clocked and ignored and row information to be integrated, both as described above—is prestored in PROM 140. This prestored pattern information is accessed by tracking the pixel lines (at counter 142) and row pattern data (at RAM 122). Note that such pattern information may be changed by computer 126. For example, if the tenth line of pixels fails to show an edge in the example discussed above, microcomputer 126 can command reading of the ninth or eleventh line The most significant bit at output Q of row pattern PROM 140 indicates end of a line or row at sensor 110, and clears pixel counter 142, enables incrementing of row counter 138, and functions through a delay at shift register 148 to access the row pattern information at RAM 122 for the next row.

In the above-described working embodiment of the invention, five pointers are initially set by microcomputer 126 in row pattern number RAM 122 corresponding to images 80a-88a. Further, row pattern number RAM 122 is commanded to integrate eight adjacent lines or rows of pixel data (at register 116 of sensor 110) for images 84a, and to integrate eight adjacent pixels (column integration at gate 117 and amplifier 118 of sensor 110) at images 82a and 86a. No integration is performed for images 80a and 88a. If data at image 88a is read and a finish edge (thread) is detected, the pointer for image 88a is decremented; if no edge is detected, the pointer for image 88a is incremented. Data for image 80a is then read, and the corresponding pointer is incremented if a thread is detected and decremented if no thread is detected. In this way, the processing electronics continue to "hunt" for lateral finish edges by either incrementing or decrementing the corresponding line pointers. Thread OD is proportional to the difference between the pointers for images 80a and 88a. The pointers for images 82a, 84a and 86a are set at 25%, 50% and 75% of such difference respectively. Row pattern RAM 122 is then updated to reflect new pointers.

The camera arrangement of FIGS. 6 and 7 thus comprises a high speed computer-controlled camera in which all of the following may be readily controlled in real time: horizontal resolution, vertical resolution, pixel sensitivity, pixel size, pixel data to be read from the array, pixel data to be loaded into the computer for further processing and analysis, and frame time. The first six of these parameters may be controlled on a pixel-by-pixel basis. It will also be appreciated that computer-controlled camera arrangement of FIGS. 6 and 7 is not limited to five scan lines 80a-88a, or to reading of a full data line. Portions of a data line would be clocked at high speed and ignored. Indeed, horizontal and vertical data could be integrated simultaneously to simulate an array of any smaller size. For example, the preferred 488×380 array would be integrated vertically by eight and horizontally by four to produce an apparent 61×95 array in which each pixel would be thirty-two (8×4) times more sensitive.

When tracking threads, one line or a few lines near the threads could remain unintegrated (high resolution), and one or more lines on each side could be integrated several times. This technique would yield information over a wider range, but with reduced data amount, if the threads move out of the high resolution area. Data lines of interest could be incremented in each frame to produce a two-dimensional image of thread contour.

The camera system of FIGS. 6-7 is not in any way limited to inspection of container finishes specifically. Indeed, it is envisioned that the camera system of FIGS. 6-7 could be readily employed to inspect other container sections, such as container sidewalls and bases, to inspection of container caps, and to inspection of other diverse items such as nuts and bolts, etc.

The invention claimed is:

1. A high-speed computer-controlled camera system comprising:
   a camera including an image array sensor containing a matrix of CCD image sensing elements arranged in a row-and-column array, a plurality of first transport registers each connected in sequence to sensing elements in one of said rows and responsive to first clock signals for loading information for associated said elements, a second transport register connected to said first transport registers in sequence for receiving image information therefrom, said first transport registers being collectively responsive to second clock signals for loading information into said second transport register corresponding to each column of said image sensing elements in sequence, output means for receiving said information from said second transport register, said second transport register being responsive to third clock signals for transmitting information in sequence to said output means, said output means being responsive to fourth clock signals for providing a video output signal from said sensor, and image processing means including input means responsive to input control signals for selectively receiving and storing image data in said video output signal, and means for selectively and independently generating said first, second, third and fourth clock signals and said input control signal for selectively integrating image data by row and column at said sensor, downloading image data from said sensor to said image processing means, and receiving and storing image data at said image processing means.

2. Apparatus for inspecting transparent containers having a central axis for variations affecting commercial acceptability of such containers, said apparatus comprising:

means for rotating a container about its central axis, a light source positioned to direct diffused light energy onto a container in said rotating means from a direction lateral to said axis, camera means positioned across said axis from said light source having a field of view which includes portions of wall surfaces of said container in said rotating means, and information processing means responsive to said camera means for obtaining information as a function of optical characteristics of the container, characterized in that said camera means comprises an image array sensor having a matrix of image sensing elements arranged in a row-and-column array and means on said sensor for selectively reading image data at said sensing elements sequentially by row and column, and in that said image processing means includes means coupled to said selectively-reading means for selectively integrating on said array image data from adjacent elements in said array, and means for reading and storing selectively integrated data output from said array sensor.

3. The apparatus set forth in claim 2 wherein said selectively-reading means comprises a plurality of first transport registers for receiving image data from corresponding columns of image sensing elements, a second transport register for receiving image data from said first transport registers by element row, and output means for selectively transmitting said image data output from said second transport register, and wherein said selectively-integrating means includes means for selectively integrating image data from adjacent rows of said sensing elements at said second transport register, and means for selectively integrating image data from adjacent columns of said sensing elements at said output means.

4. A camera system including a camera having an image array sensor with a matrix of image sensing elements arranged in a row-and-column array, means for selectively reading image data at said sensing elements sequentially by row and column, and means for projecting an image to be secured onto said array sensor; and image processing means including means coupled to said selectively-reading means for selectively integrating image data from adjacent elements in said array in said selectively-reading means, and means for reading and storing selectively integrated data from said array sensor.

5. The system set forth in claim 4 wherein said selectively-reading means comprises a plurality of first transport registers for receiving image data from corresponding rows of image sensing elements, a second transport register for receiving image data from said first transport registers by element column, and output means for selectively transmitting image data from said second transport register, and wherein said image processing means includes means for selectively integrating image data from adjacent columns of said sensing elements at said second transport register, and means for selectively integrating image data from adjacent rows of said sensing elements at said output means.

6. In a camera system which includes a camera having an image array sensor with a matrix of image sensing elements arranged in a row-and-column array, means on said array sensor for sequentially reading image data at said sensing elements by row and column to provide a video signal, and separate microprocessor-based image processing means responsive to said video signal, a method of increasing signal-to-noise ratio in said video signal while reducing processing time at said image processing means comprising the steps of:

(a) selectively integrating at said sensor image data from adjacent element in said array, and (b) transmitting such selectively integrated image data to said image processing means as said video signal.

7. The method set forth in claim 6 comprising the additional steps of:

(c) identifying image areas of interest at said sensor less than the entire area of said sensor, and (d) transmitting to said image processing means in said step (b) integrated image data from only those image areas of interest identified in said step (c).

8. A method of inspecting a container having a central axis for variations affecting commercial acceptability of such container, said method comprising the steps of:

(a) directing an optical image of a container under inspection onto an image array sensor that includes a matrix of image sensing elements arranged in a row-and-column array with columns of said array having oriented orthogonally to the container axis, a plurality of first transport registers for receiving image data from corresponding columns of image sensing elements, a second transport register for serially receiving image data from said first transport registers by element row, and output means for selectively transmitting image data output information serially from said second transport register to external information processing means, (b) identifying image data of interest by row of said image sensing elements, (c) discarding image data other than said data identified in said step (b) by
 (c1) clocking all image data from said sensing elements onto said first transport registers,
 (c2) clocking data from said first transport registers onto said second transport register up to but excluding said row of interest, and
 (c3) clocking data out of said second transport register serially through said output means without simultaneously loading said data onto said external information processing means, and then
(d) downloading said data of interest identified in said step (b) by
 (d1) clocking said image data from said row of interest from said first transport registers onto said second transport register, and then
 (d2) clocking image data on said second transport register serially through said output means to said information processing means.

9. The method set forth in claim 8 wherein said steps (c2) and (c3) are carried out at a clock frequency greater than that of said step (d1) and (d2).

10. The method set forth in claim 8 wherein said step (d) includes the step of integrating image data on said sensor for a preselected number of sensor rows of said sensing elements by performing said step (d1) the same said preselected number of times before performing said step (d2), such that image data from said preselected number of rows is integrated in said second transport register before clocking through said output means.

11. The method set forth in claim 8 wherein said step (d2) comprises the steps of clocking image data in said second transport register into said output means and separately clocking image data in said output means to said external information processing means, and wherein said step (d) includes the step of integrating image data on said sensor for a preselected number of columns of said sensing elements by clocking image data in said second transport register serially into said output means for a number of clock cycles equal to said preselected number before clocking information in said output means to said information processing means.

12. The method set forth in claim 8 comprising the additional step of locating an edge portion of the container parallel to the container axis by selectively varying said row of interest identified in said step (b) until a bright/dark transition is detected between adjacent rows.

* * * * *